United States Patent
Rafko

(10) Patent No.: US 11,083,811 B2
(45) Date of Patent: *Aug. 10, 2021

(54) SANITIZING DOOR HANDLE

(71) Applicant: KleanTouch LLC, Scottsdale, AZ (US)

(72) Inventor: Michael Rafko, Scottsdale, AZ (US)

(73) Assignee: KleanTouch LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/699,846

(22) Filed: Dec. 2, 2019

(65) Prior Publication Data

US 2020/0215218 A1  Jul. 9, 2020

Related U.S. Application Data

(60) Continuation of application No. 16/000,642, filed on Jun. 5, 2018, now Pat. No. 10,494,166, and a division of application No. 16/000,644, filed on Jun. 5, 2018, now Pat. No. 10,799,606, and a division of application No. 16/000,646, filed on Jun. 5, 2018, now Pat. No. 10,918,752, and a division of application No. 16/000,647, filed on Jun. 5, 2018, (Continued)

(51) Int. Cl.
| | |
|---|---|
| *A61L 2/18* | (2006.01) |
| *E05B 1/00* | (2006.01) |
| *A61L 2/00* | (2006.01) |
| *A61L 2/24* | (2006.01) |
| *B65D 83/20* | (2006.01) |
| *B65D 83/26* | (2006.01) |
| *B65D 83/44* | (2006.01) |

(52) U.S. Cl.
CPC .............. *A61L 2/18* (2013.01); *A61L 2/0088* (2013.01); *A61L 2/24* (2013.01); *B65D 83/20* (2013.01); *B65D 83/262* (2013.01); *B65D 83/267* (2013.01); *E05B 1/0069* (2013.01); *A61L 2202/14* (2013.01); *A61L 2202/15* (2013.01); *B65D 83/44* (2013.01); *E05B 1/003* (2013.01)

(58) Field of Classification Search
CPC ....... B05B 83/20; B05B 83/44; B05B 83/262; E05B 1/0069; A61L 2/0088; A61L 2/24; A61L 2202/14
USPC ........................................... 222/192
See application file for complete search history.

(56) References Cited

U.S. PATENT DOCUMENTS 2,977,839 A * 4/1961 Koch .................. D07B 1/12
                                                87/1
6,997,394 B1 * 2/2006 Washington ............ A61L 9/042
                                                222/192

(Continued)

*Primary Examiner* — Vishal Pancholi
(74) *Attorney, Agent, or Firm* — Toering Patents PLLC

(57) ABSTRACT

Various implementations of the invention are directed toward a sanitizing door handle and/or components of such sanitizing door handle. Some implementations of the invention are directed toward a manual sanitizing door handle while some implementations of the invention are directed toward an auto-sanitizing door handle. According to some implementations of the invention, a sanitizing fluid is dispensed directly onto an exterior surface of the sanitizing door handle in connection with an operation of the door handle to sanitize the door handle. According to some implementations of the invention, a sanitizing fluid is dispensed directly onto a user's hand(s) in connection with an operation of the door handle to sanitize the user's hand(s).

16 Claims, 6 Drawing Sheets

Related U.S. Application Data now Pat. No. 10,799,607, and a division of application No. 16/000,649, filed on Jun. 5, 2018, now Pat. No. 10,792,382, and a division of application No. 16/000,650, filed on Jun. 5, 2018, now Pat. No. 10,617,777, and a division of application No. 16/000,652, filed on Jun. 5, 2018, now Pat. No. 10,925,987.

(60) Provisional application No. 62/663,506, filed on Apr. 27, 2018.

(56) References Cited

U.S. PATENT DOCUMENTS

| | | | | |
|---|---|---|---|---|
| 8,408,423 B1* | 4/2013 | McKnight | ................ | A61L 2/14 222/192 |
| 2004/0026530 A1* | 2/2004 | Callueng | ............... | E05B 1/0069 239/69 |
| 2004/0223894 A1* | 11/2004 | Gilbert | ................. | E05B 1/0069 422/292 |
| 2004/0237255 A1* | 12/2004 | Lin | ...................... | E05B 1/0069 16/110.1 |
| 2007/0241125 A1* | 10/2007 | Muderlak | ............ | E05B 1/0069 221/71 |
| 2008/0263820 A1* | 10/2008 | Blatz | ........................ | A61L 2/18 16/110.1 |
| 2008/0305020 A1* | 12/2008 | Oshmyansky | ........ | E05B 1/0069 422/291 |
| 2010/0147974 A1* | 6/2010 | Cunningham | ........ | E05B 1/0069 239/274 |
| 2010/0294806 A1* | 11/2010 | McDowell | ............ | E05B 1/0069 422/110 |
| 2012/0144610 A1* | 6/2012 | Balzano | ................ | E05B 1/0069 15/104.92 |
| 2015/0308149 A1* | 10/2015 | Oshmyansky | ......... | A47B 95/02 222/30 |

* cited by examiner

SANITIZING DOOR HANDLE

CROSS-REFERENCE TO RELATED APPLICATIONS

This Application is a continuation application of U.S. patent application Ser. No. 16/000,642, entitled "Sanitizing Door Handle," filed on Jun. 5, 2018, now granted as U.S. Pat. No. _____; which claims priority to U.S. Provisional Patent Application No. 62/663,506, entitled "Sanitizing Door Handle," and filed on Apr. 27, 2018;

this Application is a divisional application of U.S. patent application Ser. No. 16/000,644, entitled "Sanitizing Door Handle Fluid Container Assembly," and filed on Jun. 5, 2018, which claims priority to U.S. Provisional Patent Application No. 62/663,506, entitled "Sanitizing Door Handle," and filed on Apr. 27, 2018;

this Application is a divisional application of U.S. patent application Ser. No. 16/000,646, entitled "Method for Dispensing a Fluid During Door Operation," and filed on Jun. 5, 2018, which claims priority to U.S. Provisional Patent Application No. 62/663,506, entitled "Sanitizing Door Handle," and filed on Apr. 27, 2018;

this Application is a divisional application of U.S. patent application Ser. No. 16/000,647, entitled "Handle-Mounted Distribution Manifold," and filed on Jun. 5, 2018, which claims priority to U.S. Provisional Patent Application No. 62/663,506, entitled "Sanitizing Door Handle," and filed on Apr. 27, 2018;

this Application is a divisional application of U.S. patent application Ser. No. 16/000,649, entitled "Distribution Manifold with Integrated Check Valve," and filed on Jun. 5, 2018, which claims priority to U.S. Provisional Patent Application No. 62/663,506, entitled "Sanitizing Door Handle," and filed on Apr. 27, 2018;

this Application is a divisional application of U.S. patent application Ser. No. 16/000,650, entitled "Sanitizing Door Handle with External Fluid Container," and filed on Jun. 5, 2018, which claims priority to U.S. Provisional Patent Application No. 62/663,506, entitled "Sanitizing Door Handle," and filed on Apr. 27, 2018;

this Application is a divisional application of U.S. patent application Ser. No. 16/000,652, entitled "Electronic Sanitizing Door Handle," and filed on Jun. 5, 2018, which claims priority to U.S. Provisional Patent Application No. 62/663,506, entitled "Sanitizing Door Handle," and filed on Apr. 27, 2018. Each of the foregoing patent applications is incorporated herein by reference in its entirety.

FIELD OF THE INVENTION

The invention is generally related to door handles, and more specifically to sanitizing door handles.

BACKGROUND OF THE INVENTION

Conventional door handles suffer from actual or perceived cleanliness or sanitation issues. Such door handles may include, but are not limited to, restroom door handles, medical/hospital door handles, refrigerator or other food storage door handles, hotel/motel door handles, airplane bathroom handles, school door handles, clean room door handles, and other door handles.

In some instances, door handles with improved cleanliness and/or sanitation are needed. In some instances, door handles with fluid dispensers, such as, but not limited to sanitizing fluid dispensers, are needed.

SUMMARY OF THE INVENTION

Various implementations of the invention are directed toward a sanitizing door handle and/or components of such sanitizing door handle such that the sanitizing door handle is sanitized or cleaned in some fashion. Various implementations of the invention are directed toward a manual sanitizing door handle and/or components of such sanitizing door handle. In such implementations, a user manually operates a pump that dispenses a fluid, such as, but not limited to, a sanitizing fluid, onto a grip of the sanitizing door handle. Various implementations of the invention are directed toward an auto-sanitizing door handle. In such implementations of the invention, the user operates the sanitizing door handle, and such operation automatically actuates the pump to dispense the fluid onto the grip of the sanitizing door handle. In some implementations of the invention, the fluid is dispensed directly onto an exterior of the sanitizing handle. In some implementations of the invention, the fluid is dispensed into an interior of the sanitizing handle and flows through to the exterior of the sanitizing handle. In various implementations of the invention, the fluid selected for use with various implementations of the invention controls, in part, the level of "cleaning" or "sanitizing" of the door handle from sterilized to disinfected to cleaned or to some other level of cleanliness.

Various implementations of the invention are directed to a hand sanitizing dispenser that dispenses a fluid, such as a sanitizing fluid, onto hand(s) of a user when the user operates or otherwise engages a door handle, such as, but not limited to, the sanitizing door handles discussed above. In some implementations of the invention, the fluid is dispensed directly onto the hands of the user. In some implementations of the invention, the fluid is dispensed onto the exterior of the sanitizing handle and is subsequently passed onto the hands of the user through contact with the sanitizing door handle. In some implementations of the invention, the fluid is dispensed into an interior of the sanitizing handle, flows through to the exterior of the sanitizing handle, and subsequently is passed onto the hands of the user through contact with the sanitizing door handle. In various implementations of the invention, the fluid selected for use with various implementations of the invention controls, in part, the level of "cleaning" or "sanitizing" of the hands of the user from sterilized to disinfected to cleaned or to some other level of cleanliness.

DETAILED DESCRIPTION

Various implementations of the invention are directed toward a sanitizing door handle and/or components of such sanitizing door handle such that the sanitizing door handle is sanitized or cleaned in some fashion. Various implementations of the invention are directed toward a manual sanitizing door handle and/or components of such sanitizing door handle. In such implementations, a user manually operates a pump that dispenses a fluid, such as, but not limited to, a sanitizing fluid, onto a grip of the sanitizing door handle. Various implementations of the invention are directed toward an auto-sanitizing door handle. In such implementations of the invention, the user operates the sanitizing door handle, and such operation automatically actuates the pump to dispense the fluid onto the grip of the sanitizing door handle. In some implementations of the invention, the fluid is dispensed directly onto an exterior of the sanitizing handle. In some implementations of the invention, the fluid is dispensed into an interior of the sanitizing handle and flows through to the exterior of the sanitizing handle. In various implementations of the invention, the fluid selected for use with various implementations of the invention controls, in part, the level of "cleaning" or "sanitizing" of the door handle from sterilized to disinfected to cleaned or to some other level of cleanliness.

Various implementations of the invention are directed to a hand sanitizing dispenser that dispenses a fluid, such as a sanitizing fluid, onto hand(s) of a user when the user operates or otherwise engages a door handle, such as, but not limited to, the sanitizing door handles discussed above. In some implementations of the invention, the fluid is dispensed directly onto the hands of the user. In some implementations of the invention, the fluid is dispensed onto the exterior of the sanitizing handle and is subsequently passed onto the hands of the user through contact with the sanitizing door handle. In some implementations of the invention, the fluid is dispensed into an interior of the sanitizing handle, flows through to the exterior of the sanitizing handle, and subsequently is passed onto the hands of the user through contact with the sanitizing door handle. In various implementations of the invention, the fluid selected for use with various implementations of the invention controls, in part, the level of "cleaning" or "sanitizing" of the hands of the user from sterilized to disinfected to cleaned or to some other level of cleanliness.

These, and other implementations and/or inventions and/or components thereof are now described.

Sanitizing Door Handle

Figure 1:
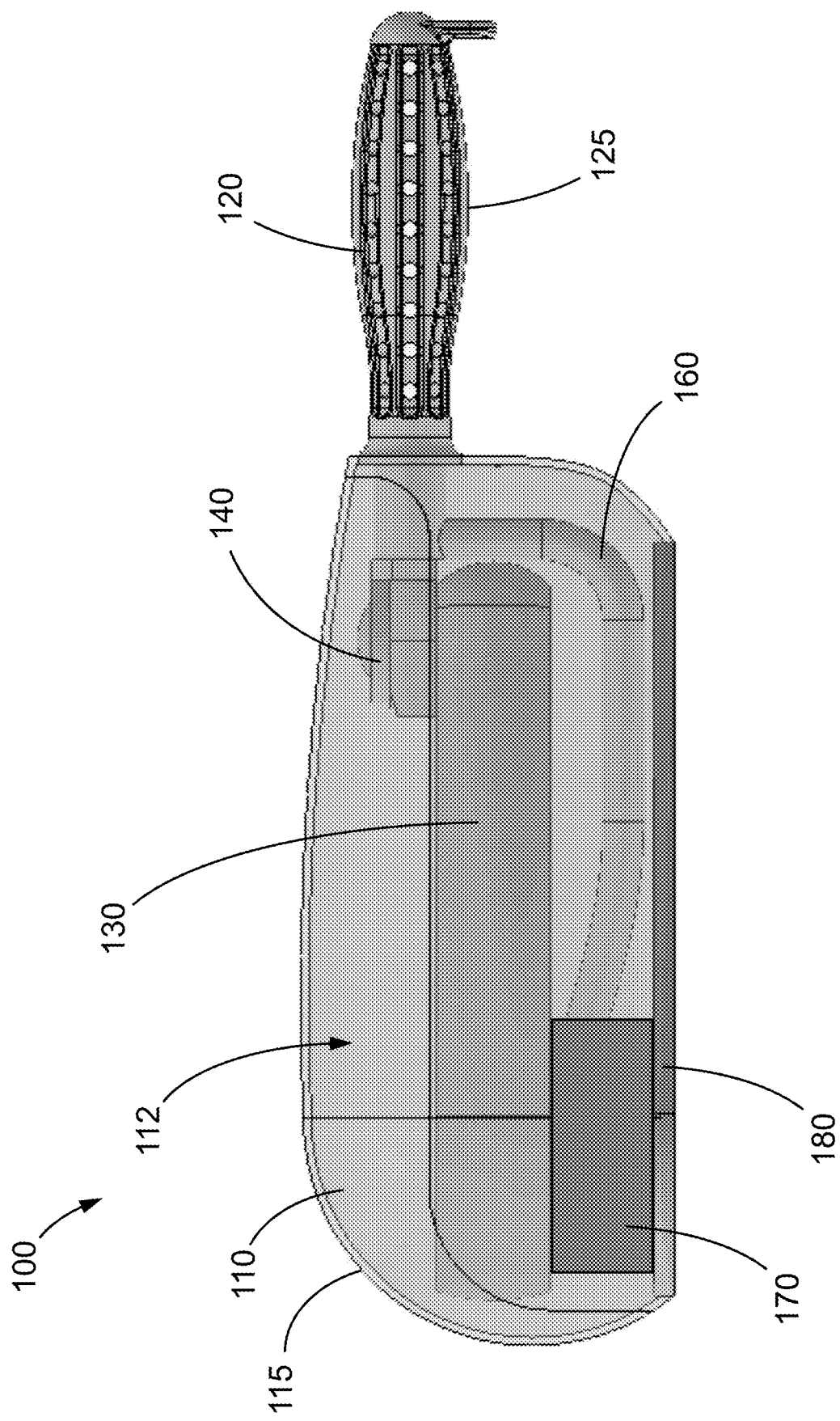
FIG. 1 illustrates a sanitizing door handle from a first perspective in accordance with various implementations of the invention.
Figure 2:
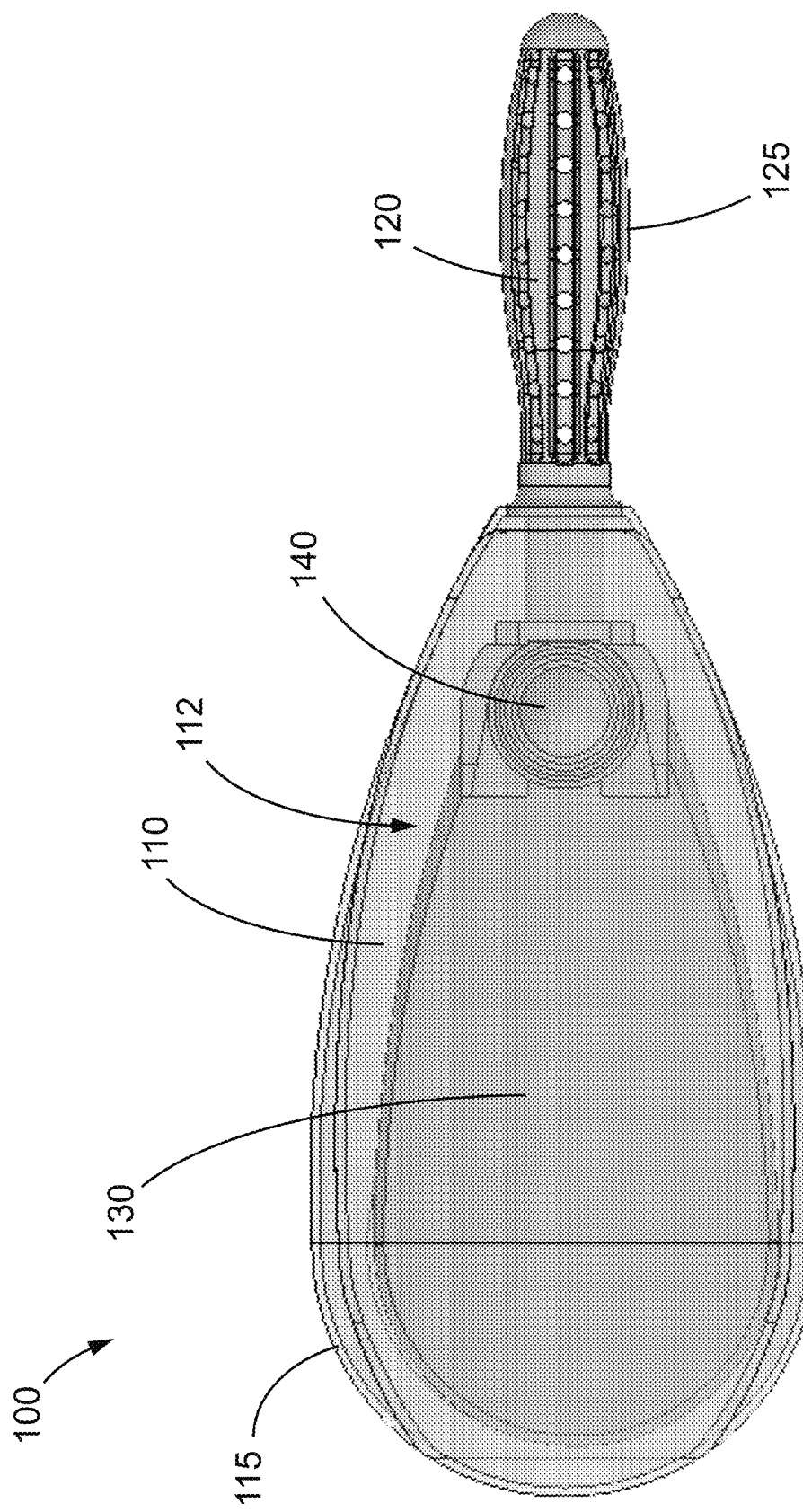
FIG. 2 illustrates a sanitizing door handle from a second perspective in accordance with various implementations of the invention.

FIG. 1 illustrates a sanitizing door handle 100 from a first perspective according to various implementations of the invention. FIG. 2 illustrates sanitizing door handle 100 from a second perspective according to various implementations of the invention. Door handle 100 includes a door handle housing 110 having a housing wall 115. Housing wall 115 may be fabricated from a variety of materials, including, but not limited to: metal, plastic, ceramic, fiberglass, wood, polymer, rubber, or other materials that may be used to fabricate housing wall 115, and/or combinations thereof, as would be appreciated. Housing wall 115 forms a hollow interior housing chamber 112 of door handle housing 110. Housing wall 115 may be formed from one or more housing wall components. In some implementations of the invention, at least one housing wall component is detachable from housing wall 115 in order to provide access to interior housing chamber 112. In some implementations of the invention, housing wall 115 is detachable from a door in order to provide access to interior housing chamber 112. Interior housing chamber 112 and its purpose is described in further detail below.

Door handle 100 may be configured as a grip, a knob, a lever, a button, a pushbar, a pullbar, a latch, or other suitable handle by which a user opens, closes, latches, unlatches, locks, unlocks, or otherwise operates door handle 100 to open or close a door to which door handle 100 is operatively attached. In some implementations of the invention, door handle 100 may be configured to push open the door. In some implementations of the invention, door handle 100 may be configured to pull open the door. In some implementations of the invention, door handle 100 may be configured to push to actuate a latch to open the door. In some implementations of the invention, door handle 100 may be configured to pull to actuate the latch to open the door. In some implementations of the invention, door handle 100 may be configured to rotate up to open the door. In some implementations of the invention, door handle 100 may be configured to rotate down to open the door. In some implementations of the invention, door handle 100 may be configured to rotate up to actuate the latch to open the door. In some implementations of the invention, door handle 100 may be configured to rotate down to actuate the latch to open the door. In some implementations of the invention, door handle 100 may be configured to slide left to open the door. In some implementations of the invention, door handle 100 may be configured to slide right to open the door. In some implementations of the invention, door handle 100 may be configured to slide left to actuate the latch to open the door. In some implementations of the invention, door handle 100 may be configured to slide right to actuate the latch to open the door. In some implementations of the invention, door handle 100 may be configured to be depressed to open the door. In some implementations of the invention, door handle 100 may be configured to be depressed to actuate the latch to open the door. In some implementations of the invention, door handle 100 may be configured to open the door or actuate the latch in other manners as would be appreciated.

According to various implementations of the invention, door handle 100 includes a door handle grip 120. In some implementations of the invention, door handle grip 120 may be fabricated from a variety of materials, including, but not limited to: metal (e.g., aluminum, titanium, stainless steel, etc.), plastic, polymer, ceramic, fiberglass, wood, rubber, other materials that may be used to fabricate door handle grip 120, and/or combinations thereof (e.g., polymer coated metal, etc.), as would be appreciated.

In some implementations of the invention, door handle grip 120 is operatively coupled to, for example, a door latch linkage 160 and/or a door latch actuator 170 as illustrated in FIG. 1 and FIG. 2. As would be appreciated, door latch actuator 170 operatively engages a door latch which in turn allows a door to open and/or close as would be appreciated. In some implementations of the invention, door latch linkage 160 may also be operatively coupled to a pump actuator (not otherwise illustrated) configured to, mechanically or electronically, actuate fluid pump 140 when the user operates door handle 100 via door handle grip 120 as would be appreciated.

According to various implementations of the invention, when the user operates door handle 100 via door handle grip 120, a fluid is dispensed onto door handle grip 120. In some implementations of the invention, the fluid is a sanitizing fluid that is dispensed onto door handle grip 120 to sanitize door handle grip 120. In some implementations of the invention, the sanitizing fluid is dispensed directly onto door handle grip 120 to sanitize door handle grip 120. In some implementations of the invention, the sanitizing fluid is dispensed into an interior of door handle grip 120 and flows through door handle grip 120 to sanitize door handle grip 120. In various implementations of the invention, the sanitizing fluid may be dispensed onto door handle grip 120, before, during, and/or after the operation of door handle 100 by the user.

According to various implementations of the invention, when the user operates door handle 100 via door handle grip 120, a fluid is dispensed onto the hand(s) of the user. In some implementations of the invention, the fluid is a sanitizing fluid that is dispensed onto the hand(s) of the user to sanitize the hand(s). In some implementations of the invention, the sanitizing fluid is dispensed directly onto the hand(s) of the user to sanitize the hand(s). In some implementations of the invention, the sanitizing fluid is dispensed directly onto door handle grip 120 to sanitize the hand(s) of the user when the hand(s) come into contact with handle grip 120. In some implementations of the invention, the sanitizing fluid is dispensed into an interior of door handle grip 120 and flows through door handle grip 120 to sanitize the hand(s) of the user when the hand(s) come into contact with handle grip 120. In various implementations of the invention, the sanitizing fluid may come into contact with the hand(s) before, during, and/or after the operation of door handle 100 by the user.

Fluid Container Assembly

Figure 3:
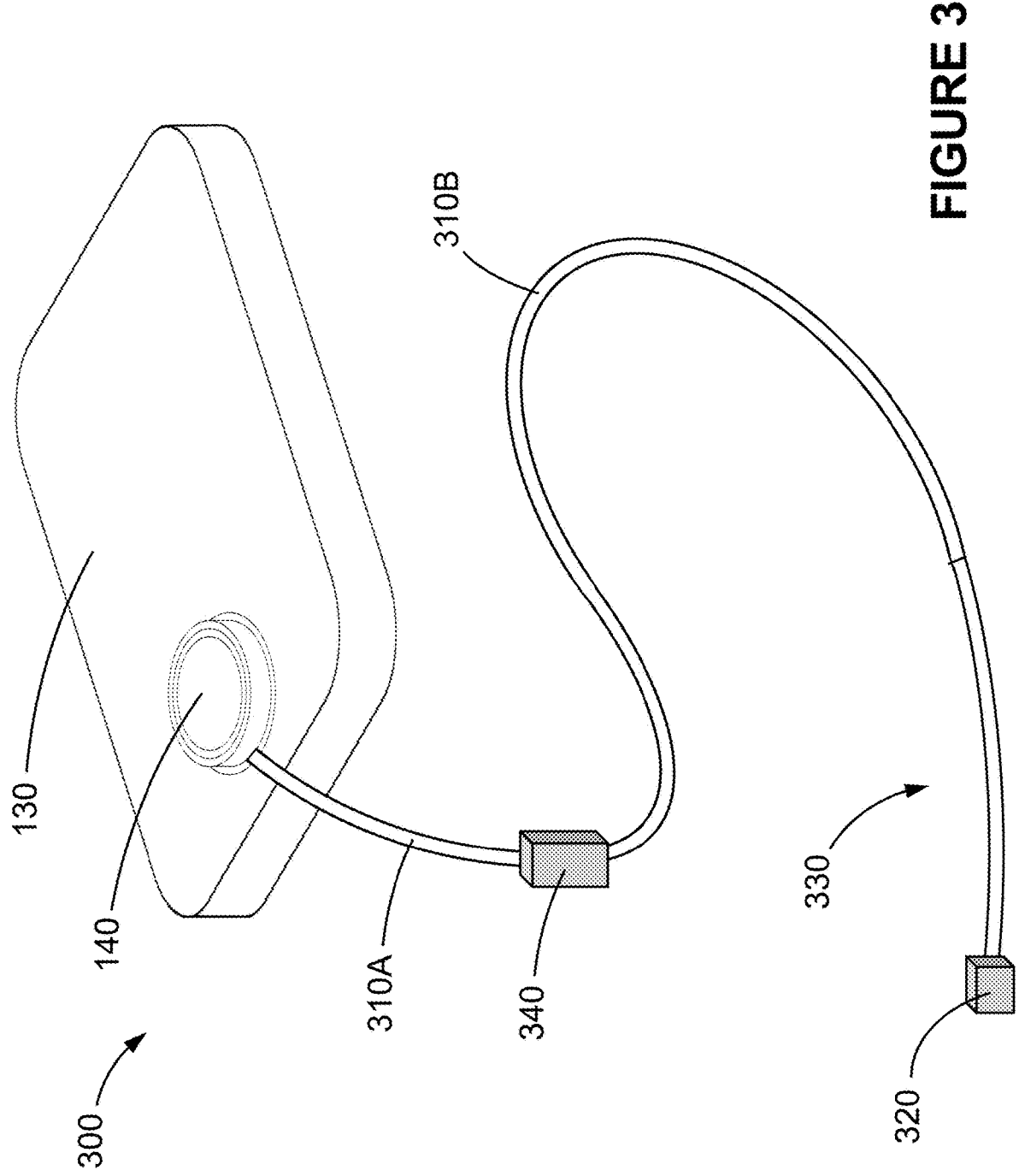
FIG. 3 illustrates a sanitizing fluid assembly in accordance with various implementations of the invention.

In some implementations of the invention, door handle 100 includes a fluid container assembly disposed in interior housing chamber 112. FIG. 3 illustrates a fluid container assembly 300 according to various implementations of the invention. (Various components of fluid container assembly 300, such as fluid container 130 and a fluid pump 140, are also illustrated in FIG. 1 and FIG. 2 in an exemplary configuration.) In some implementations of the invention, fluid container assembly 300 may include fluid container 130, fluid pump 140, one or more sections of tubing 310 (illustrated in FIG. 3, for example, as tubing 310A and tubing 310B). In some implementations of the invention, fluid container assembly 300 may also include a distribution manifold 330. In some implementations of the invention, fluid container assembly 300 may also include a tubing cap 320 or other termination. In some implementations of the invention, fluid container assembly 300 may also include a check valve 350.

According to various implementations of the invention, fluid pump 140 is coupled to fluid container 130 and configured to pump a fluid (not otherwise illustrated) from inside of fluid container 130 into tubing 310. In some implementations of the invention, tubing 310 is operatively coupled to fluid pump 140; however, in other implementations of the invention, tubing 310 may be operatively coupled directly to fluid container 130 as would be appreciated. In some implementations of the invention such as that illustrated in the drawings, fluid pump 140 is a diaphragm pump which operates by mechanically depressing the diaphragm of fluid pump 140 to force some amount of the fluid out of fluid container 130, through fluid pump 140, and into tubing 310. In some implementations of the invention, other types of pumps may be used, including various other mechanical type or electrical type pumps. In some implementations of the invention, fluid pump 140 may be manually actuated by the user; for example, the user may depress the diaphragm of fluid pump 140 to fluid actuate pump 140. In some implementations of the invention, fluid pump 140 may be indirectly actuated by the user; for example, fluid pump 140 may be indirectly and automatically actuated when the user operates door handle 100, either via cams, levers, linkages, etc., to mechanically actuate fluid pump 140, or via a switch to electrically actuate fluid pump 140, as would be appreciated.

In some implementations of the invention, the fluid may be a sanitizing fluid, which may include any fluid having sterilizing, disinfecting, antiseptic, antimicrobial, and/or other sanitizing or cleaning properties. Active ingredients in the sanitizing fluid may include alcohol-based sanitizing fluids such as, but not limited to, isopropyl alcohol, ethyl alcohol, n-proponal, and other alcohol-based fluids; or non-alcohol-based sanitizing fluids such as, but not limited to, benzalkonium chloride (a chemical disinfectant), triclosan (an antiseptic), thymol (an organic antibacterial agent), and/or other non-alcohol-based sanitizing fluids. In some implementations of the invention, the active ingredients may be mixed with a carrier ingredient such as glycerol or other gel-like ingredient to achieve a certain amount of viscosity as would be appreciated. In some implementations of the invention, the active ingredients may be aerosolized to be sprayed onto hand(s) or door handles as would be appreciated. Sanitizing fluids are available from various manufacturers and sold under names, including, but not limited to: Purell®, Germ-X®, CleanWell™, Babyganics®, CVS®, BlumNaturals®, and other manufacturers and/or names.

In some implementations of the invention, tubing 310 facilitates transport of sanitizing fluid from fluid container 130 through distribution manifold 330 to door handle grip 120. In some implementations of the invention, tubing 310 facilitates transport of sanitizing fluid from fluid container 130 to door handle grip 120; in such implementations, door handle grip 120 incorporates distribution manifold 330 or door handle grip 120 functions on its own in a manner similar to distribution manifold 330. In various implementations, tubing 310 may include, but is not limited to: nylon tubing, vinyl tubing, pvc tubing, rubber tubing, Teflon tubing, Tyron tubing, hdpe tubing, PFA tubing, FEP tubing, MFA tubing, PTFE tubing and other types of tubing as would be appreciated.

Distribution Manifold

Figure 5:
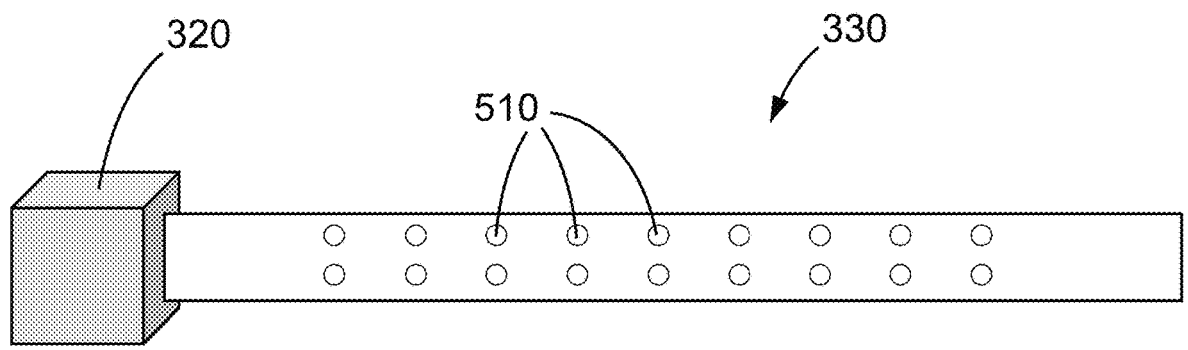
FIG. 5 illustrates a distribution manifold in accordance with various implementations of invention.

FIG. 5 illustrates distribution manifold 330 in further detail. In some implementations of the invention, distribution manifold 330 is formed separate from and then coupled to tubing 310. In some implementations of the invention, distribution manifold 330 is formed as part of tubing 310. According to various implementations of the invention, distribution manifold 330 dispenses fluid from an interior of distribution manifold 330 to an exterior of distribution manifold 330 via a plurality of distribution holes, such as distribution holes 510 in FIG. 5. In some implementations of the invention, distribution holes 510 are formed around a circumference of distribution manifold 330. In some implementations of the invention, distribution holes 510 are formed along a length of distribution manifold 330. In some implementations of the invention, distribution holes 510 are formed along the circumference and the length of distribution manifold 330. In some implementations of the invention, distribution holes 510 are formed only along a portion of the circumference and/or a portion of the length of distribution manifold 330. In some implementations of the invention, a single distribution hole 510 may be used. In some implementations of the invention, a plurality of distribution holes 510 may be used. Various numbers of distribution holes 510 may be used and configured in various patterns as would be appreciated. In some implementations of the invention, distribution manifold 330 may be terminated (i.e., closed such that no fluid may exit its end). In some implementations of the invention, distribution manifold 330 may be terminated by a tubing cap 520.

In some implementations of the invention, distribution holes 510 are sized based on various fluid parameters of the sanitizing fluid, for example, viscosity, evaporation rate, density, and/or other various fluid parameters. In some implementations of the invention, distribution holes 510 may be "self-healing" in the sense that when the sanitizing fluid in distribution manifold 330 is under pressure (e.g., pressure created by fluid pump 140), distribution holes 510 open, allowing sanitizing fluid to be dispensed; and when the sanitizing fluid in distribution manifold 330 is not under pressure, distribution holes 510 close, allowing little, if any, sanitizing fluid to be dispensed. Such self-healing implementations may be configured using, for example, nylon tubing, or the like, as would be appreciated. In some implementations of the invention, distribution manifold 330 is coupled to and/or disposed within door handle grip 120.

In some implementations of the invention, fluid container assembly 300 is a replacement fluid container assembly 300 such that once the fluid is emptied from fluid container assembly 300, such an "empty" fluid container assembly 300 may be removed from door handle 100, and a new fluid container assembly 300 may be installed in door handle 100. In some implementations of the invention, fluid container assembly 300 may be sold together with door handle 100; while in some implementations of the invention, fluid container assembly 300 may be sold separately from door handle 100 as would be appreciated. In some implementations of the invention, fluid container 130 may be refillable without replacing fluid container assembly 300.

Door Handle Grip

Figure 4:
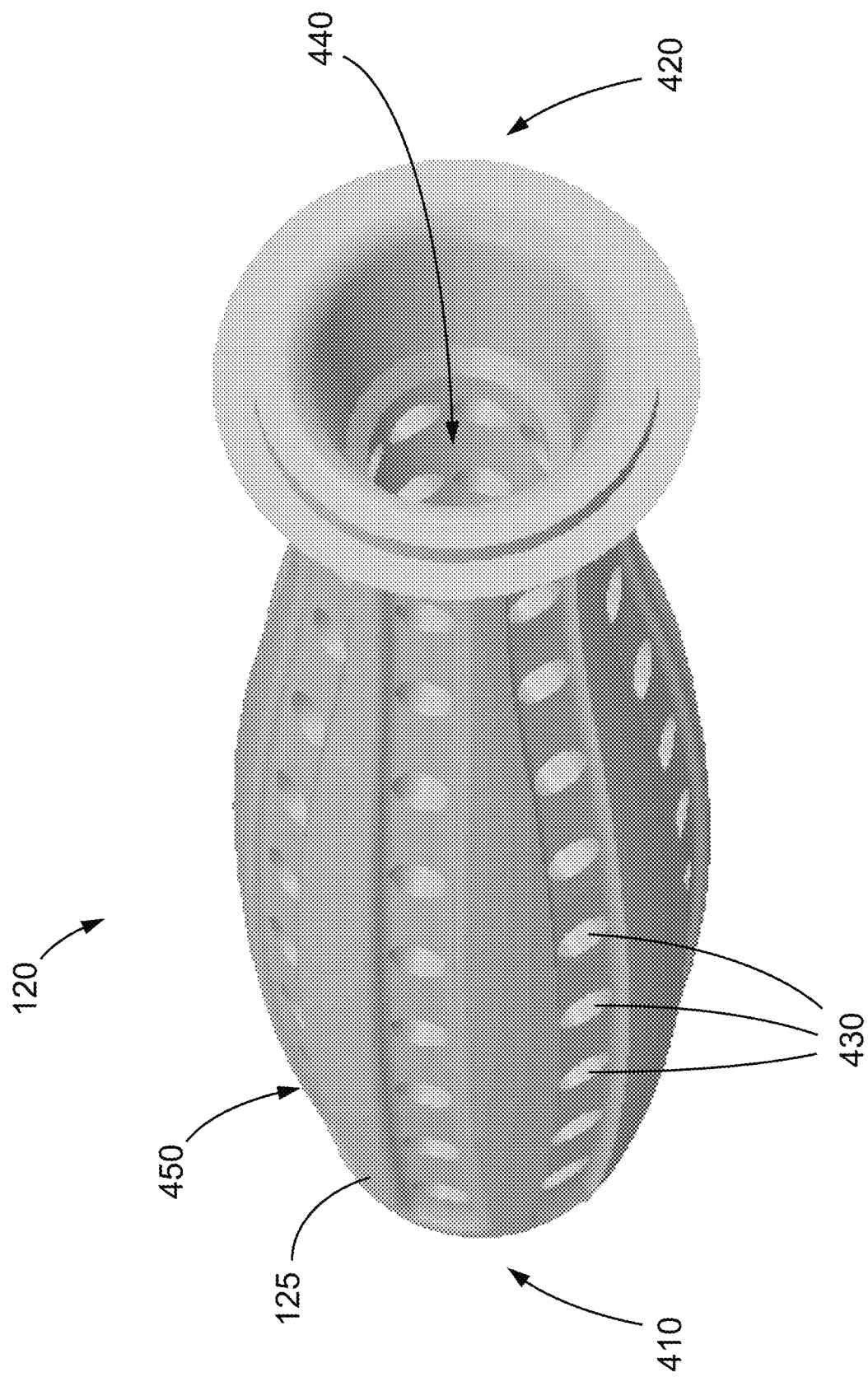
FIG. 4 illustrates a door handle grip in accordance with various implementations of invention.

FIG. 4 illustrates door handle grip 120 in further detail. Door handle grip includes a distal grip end 410 and a proximal grip end 420. In some implementations of the invention, grip wall 125 forms a hollow interior grip chamber 440 extending from proximal grip end 420 to distal grip end 410. In some implementations of the invention, distal grip end 410 is closed and proximal grip end 420 is open. In some implementations of the invention, both ends 410, 420 are open. While door handle grip 120 is illustrated as generally cylindrical in FIG. 4, other shapes and configurations may be used. For example, door handle grip 120 may be configured to conform with any shape of a door interface with which the user comes into contact to operate door handle 100, including configured to conform entirely around such door interface, partially around such door interface, or simply on one or more surfaces of such door interface, as would be appreciated.

In some implementations of the invention, a plurality of grip holes (illustrated, for example, as a plurality of grip holes 430 in FIG. 4) are formed into grip wall 125. In some implementations of the invention, grip holes 430 serve to transfer the fluid from interior grip chamber 440 to an exterior grip surface 450 of door handle grip 120. In this way, the fluid entering interior grip chamber 440 from proximal grip end 440 is dispensed through interior grip chamber 440, through grip holes 430 and onto exterior grip surface 450. In some implementations of the invention, grip holes 430 are located on door handle grip 120 in regions where the user is likely to engage door handle 100 in order to operate door handle 100. In some implementations of the invention, grip holes 430 are formed around a circumference of door handle grip 120. In some implementations of the invention, grip holes 430 are formed along a length of door handle grip 120. In some implementations of the invention, grip holes 430 are formed along the circumference and the length of door handle grip 120. In some implementations of the invention, grip holes 430 are formed only along a portion of the circumference and/or a portion of the length of door handle grip 120. In some implementations of the invention, a single grip hole 430 may be used. In some implementations of the invention, a plurality of grip holes 430 may be used. In some implementations of the invention, grip holes 430 are formed in a length of about a hand's width (e.g., 3-6 inches). In some implementations of the invention, grip holes 430 are formed in a length of about two hand's width (e.g., 6-12 inches). Other lengths of grip holes 430 along door handle grip 120 may be used as would be appreciated. Various numbers of grip holes 430 may be used and configured in various patterns as would be appreciated.

In some implementations of the invention, distribution manifold 330 is operatively coupled to door handle grip 120. In some implementations of the invention, distribution manifold 330 is disposed in interior grip chamber 440 of door handle grip 120. In such implementations, when the fluid is dispensed through distribution manifold 330, the fluid enters interior grip chamber 440 of door handle grip 120 and is subsequently dispensed through grip holes 430 to exterior grip surface 450 of door handle grip 120. In some implementations of the invention, distribution holes 510 are aligned with grip holes 430 to facilitate flow of the fluid through distribution manifold 330 to exterior grip surface 450 of door handle grip 120 as would be appreciated.

In some implementations of the invention, distribution manifold 330 is integrated directly into door handle grip 120. In such implementations, tubing 310 is operatively coupled to door handle grip 120 which in turn functions as both grip and distribution manifold as discussed above.

Check Valve

In some implementations of the invention, check valve 340 is coupled between fluid pump 140 and distribution manifold 330. In some implementations of the invention, check valve 340 is coupled directly to fluid pump 140. In some implementations of the invention, check valve 340 is coupled directly to distribution manifold 330. In some implementations of the invention, check valve 340 is coupled to tubing 310 in between pump 140 and distribution manifold 330 (i.e., check valve 340 coupled between tubing 310A and 310B as illustrated in FIG. 3).

According to various implementations of the invention, check valve 340 is configured to allow the fluid from fluid container 130 to flow in only one direction, namely from fluid container 130 to distribution manifold 330. When actuated, fluid pump 140 pumps (i.e., forces) the fluid from fluid container 130 into tubing 310, through check valve 340 and on toward distribution manifold 330. Once pressure from fluid pump 140 subsides, check valve 340 closes to prevent the fluid from flowing back to fluid container 130 and also to maintain pressure in tubing 310 between check valve 340 and distribution manifold 330 until the fluid is dispensed.

Figure 6:
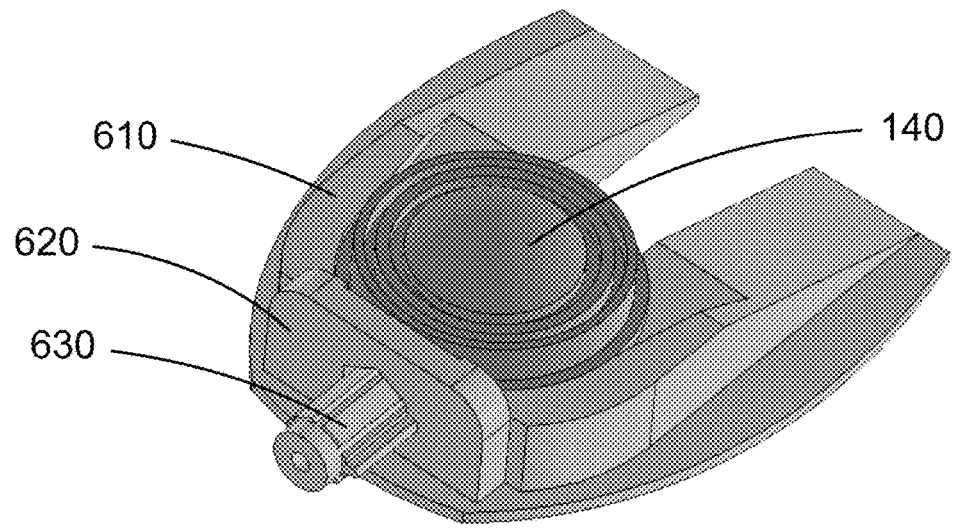
FIG. 6 illustrates a fluid pump and a keyed check valve in accordance with various implementations of the invention.
Figure 7:
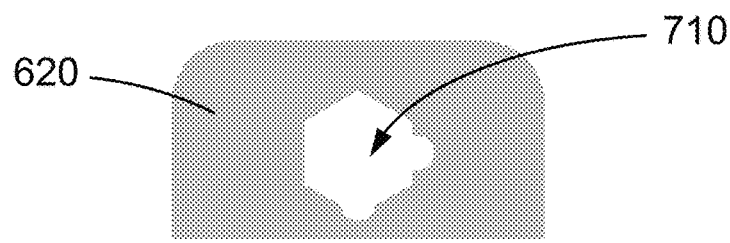
FIG. 7 illustrates a keyed check valve receiver in accordance with various implementations of the invention.

In some implementations of the invention, check valve 340 may be shaped or "keyed" to aid in aligning or positioning various components of fluid container assembly 300 in door handle 100. For example, FIG. 6 illustrates fluid pump 140 coupled to a keyed check valve 630 in accordance with various implementations of the invention. In some implementations of the invention, a pump seat 610 may be integrated into interior housing chamber 112 to align, orient and/or position fluid pump 140 in interior housing chamber 112. As illustrated, pump seat 610 may include a keyed check valve receiver 620. In some implementations of the invention, only keyed check valve 630 may fit into keyed check valve receiver 620. FIG. 7 illustrates an example of a keyed hole 710 formed in keyed check valve receiver 620 configured to receive keyed check valve 630. As would be appreciated, keyed hole 710 and keyed check valve 630 may have corresponding shapes different from that illustrated in FIG. 7. For example, while keyed hole 710 (and corresponding keyed check valve 630) is illustrated as generally hexagon and isometric in shape, keyed hole 710 may be other than generally hexagonal in shape or other than generally isometric in shape. Also for example, while keyed hole 710 is illustrated as having two semicircular protrusions, keyed hole 710 may have other numbers of protrusions or other indentations (e.g., semicircular indentations) as would be appreciated. In some implementations of the invention, keyed check valve 630 may be friction fit into keyed hole 710 as would be appreciated. In some implementations of the invention, keyed check valve 630 may be snap fit into keyed hole 710 as would be appreciated.

In some implementations of the invention (not otherwise illustrated), keyed check valve 630 may be directly coupled to distribution manifold 330. In such implementations, keyed check valve receiver 620 may be integrated into door handle grip 120 to align, orient, and/or position distribution manifold 330 in door handle grip. In some implementations of the invention (not otherwise illustrated), keyed check valve 630 and keyed check valve receiver 630 may be disposed at various locations in door handle 100 to maintain alignment, orientation, and/or position of various components of fluid container assembly 300 as would be appreciated.

While keyed check valve 630 is described herein as a single component, it may be separated into two separate components, namely a check valve and a key, as would be appreciated. While fluid pump 140 and keyed check valve 630 are illustrated in FIG. 6 as being directly coupled to one another, in other implementations, tubing 310 may be disposed between fluid pump 140 and keyed check valve 630 as would be appreciated.

Tubing Cap

In some implementations of the invention, tubing cap 320 is shaped or "keyed" to a corresponding key hole in distal end 410 of interior grip chamber 440 of door handle grip 120. In some implementations of the invention, tubing cap 320 is sized to friction fit or snap fit tubing cap 320 into the key hole of interior grip chamber 440 of door handle grip 120 to maintain alignment, orientation, and/or position of distribution manifold 330 within interior grip chamber 440 as would be appreciated.

Fluid Container Housing External to Door Handle

Figure 8:
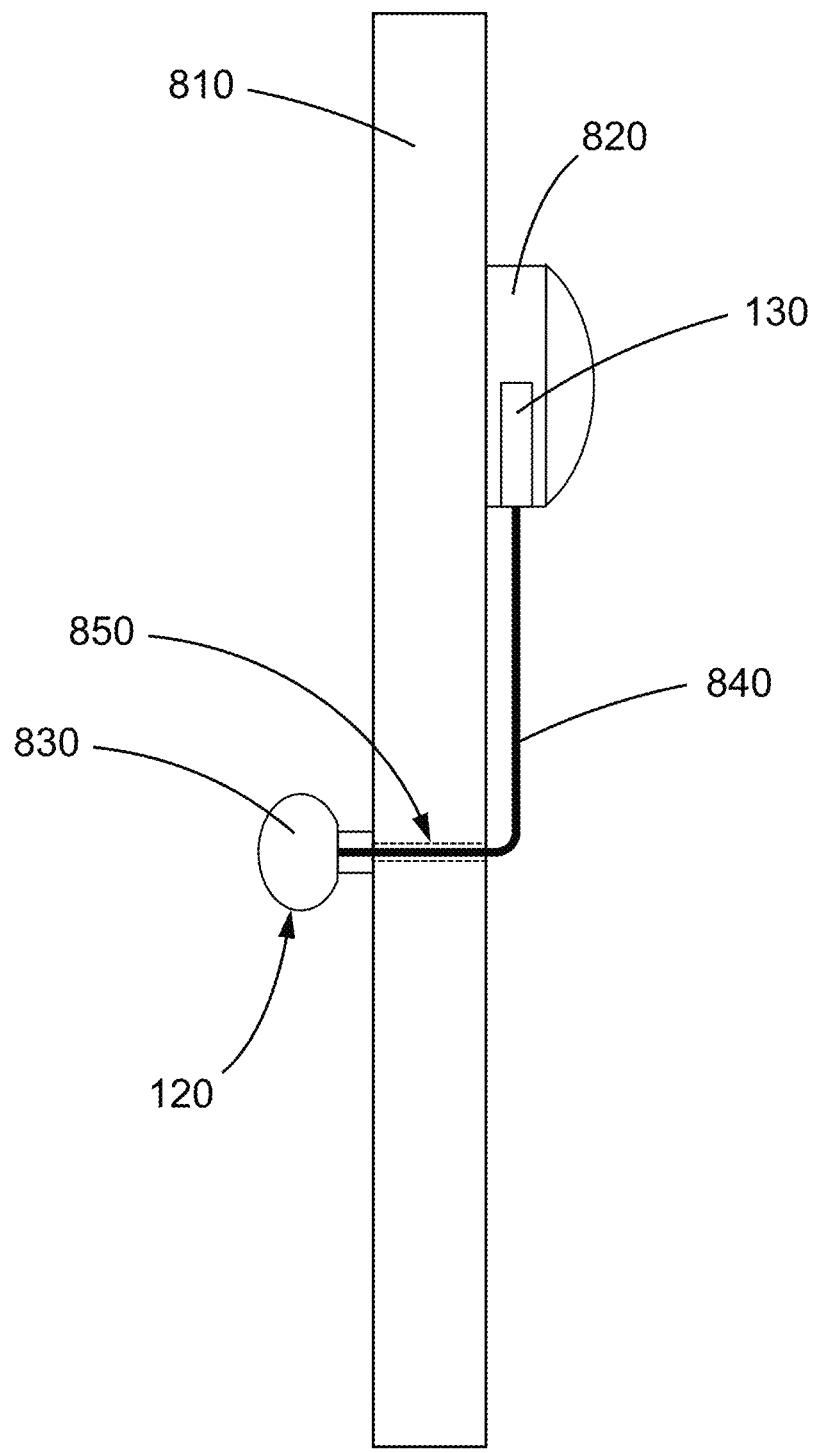
FIG. 8 illustrates a fluid container housing separate from a door handle in accordance with various implementations of the invention.

In various implementations of the invention, fluid container 130 (and associated components) are disposed externally to a door handle. FIG. 8 illustrates a fluid container housing 820, including fluid container 130, separate from and external to a door handle 830 in accordance with various implementations of the invention. Such implementations may be desirable in situations where space, access, clearance and/or configuration considerations do not permit installation of door handle 100. In these implementations of the invention, fluid container housing 820 houses fluid container 130 and other components of fluid container assembly 300 (not otherwise illustrated in FIG. 8) as would be appreciated. Fluid container 130 is operatively coupled to external tubing 840, which in some implementations of the invention, may be covered, for example, with braided reinforcement to protect external tubing 840 as would be appreciated. In some implementations of the invention, fluid container housing is mounted on the same side of a door 810 as door handle 830. In some implementations of the invention, fluid container housing is mounted on the opposite side of door 810 as door handle 830. In some implementations of the invention, fluid container housing is mounted on a wall (not otherwise illustrated in FIG. 8) near door 810 on either the same or opposite side of door 810 as door handle 830. Depending on which side of door 810 fluid container housing 820 is mounted in relation to door handle 830, external tubing 840 may be configured to pass through a hole 850 in door 810, such as is illustrated in FIG. 8. Then, in a manner similar to that described above, external tubing 840 is operatively coupled to door handle grip 120 surrounding door handle 830. These implementations of the invention may utilize a battery-operated electrical pump disposed in or proximate to fluid container housing 820 and a switch disposed in door handle 830 or in door handle grip 120 for purposes of dispensing fluid from fluid container 130 to exterior grip surface 450 of door handle grip 120.

While various implementations of the invention have been described herein in reference to certain door handles illustrated in the drawings, for example, other door handles and configurations thereof may be used as would be appreciated.

What is claimed:

1. A door handle comprising:
    a door handle housing comprising a housing wall, wherein the housing wall forms an interior housing chamber, wherein the door handle housing is configured to be operatively mounted to a door;
    a door handle grip coupled to the door handle housing, the door handle grip comprising a grip wall, wherein the grip wall forms an interior grip chamber, wherein the interior housing chamber of the housing wall and the interior grip chamber of the grip wall are in communication with one another, wherein the grip wall also forms a plurality of grip holes that communicate the interior grip chamber of the grip wall with an exterior surface of the grip wall;
    a fluid container disposed in the interior housing chamber of the housing wall;
    a tubing having a first end and second end, wherein the first end of the tubing is configured to receive a fluid from the fluid container and to communicate the fluid to the second end of the tubing, wherein the door handle grip is configured to receive the fluid from the second end of the tubing;
    a pump configured to force the fluid out of the fluid container into the first end of the tubing, through the tubing to the second end of the tubing, into the interior grip chamber of the door handle grip, through the plurality of grip holes and onto an exterior of the grip wall.

2. The door handle of claim 1, further comprising a door latch actuator operatively coupled to the door handle.

3. The door handle of claim 2, further comprising a door latch linkage operatively coupling the door latch actuator to the door handle.

4. The door handle of claim 1, wherein the fluid container comprises a sterilizing, disinfecting, antiseptic, antimicrobial, sanitizing or cleaning fluid.

5. The door handle of claim 1, wherein the fluid container comprises an alcohol-based sanitizing fluid.

6. The door handle of claim 1, wherein the fluid container comprises a non-alcohol-based sanitizing fluid.

7. The door handle of claim 4, wherein the fluid comprises a gel-like carrier ingredient.

8. The door handle of claim 1, wherein the fluid container is refillable.

9. The door handle of claim 1, wherein the fluid container is replaceable.

10. The door handle of claim 1, wherein the fluid container and tubing are replaceable.

11. The door handle of claim 1, further comprising a distribution manifold coupled to the second end of the tubing, wherein the distribution manifold communicates fluid from an interior of the distribution manifold to an exterior of the distribution manifold via a plurality of distribution holes.

12. The door handle of claim 11, wherein the distribution manifold is formed into the second end of the tubing.

13. The door handle of claim 1, further comprising a check valve disposed along the tubing between the fluid container and the second end of the tubing, the check valve configured to permit flow of the fluid through the tubing from the fluid container to the second end of the tubing and to inhibit flow of the fluid through the tubing back to the fluid container.

14. The door handle of claim 1, wherein the pump is a mechanically actuated pump.

15. The door handle of claim 1, wherein the pump is a electrically actuated pump.

16. The door handle of claim 1, wherein the pump is actuated when a user operates the door handle.

\* \* \* \* \*